United States Patent
Benovsky et al.

(10) Patent No.: US 7,601,741 B2
(45) Date of Patent: Oct. 13, 2009

(54) PROCESS FOR MAKING MONTELUKAST AND INTERMEDIATES THEREFOR

(75) Inventors: Petr Benovsky, Brno (CZ); Lambertus Thijs, Wijchen (NL); Arjanne Overeem, Ede (NL); Jakub Castulik, Brno (CZ); Jie Zhu, Nijmegen (NL); Petr Bartos, Brno (CZ); Radomir Skoumal, Blansko (CZ)

(73) Assignee: Synthon BV, Nijmegen (NL)

( * ) Notice: Subject to any disclaimer, the term of this patent is extended or adjusted under 35 U.S.C. 154(b) by 9 days.

(21) Appl. No.: 11/561,724

(22) Filed: Nov. 20, 2006

(65) Prior Publication Data

US 2007/0135643 A1 Jun. 14, 2007

Related U.S. Application Data

(60) Provisional application No. 60/737,752, filed on Nov. 18, 2005, provisional application No. 60/794,429, filed on Apr. 24, 2006, provisional application No. 60/824,382, filed on Sep. 1, 2006.

(51) Int. Cl.
*C07D 215/18* (2006.01)
*A61K 31/47* (2006.01)

(52) U.S. Cl. .................................. 514/311; 546/180
(58) Field of Classification Search ............... 546/180; 514/311
See application file for complete search history.

(56) References Cited

U.S. PATENT DOCUMENTS

| | | | |
|---|---|---|---|
| 4,999,362 A * | 3/1991 | Gandolfi et al. | ............. 514/334 |
| 5,266,568 A | 11/1993 | Belley et al. | |
| 5,270,324 A | 12/1993 | Zamboni et al. | |
| 5,523,477 A | 6/1996 | King et al. | |
| 5,565,473 A | 10/1996 | Belley et al. | |
| 5,585,115 A | 12/1996 | Sherwood et al. | |
| 5,614,632 A | 3/1997 | Bhupathy et al. | |
| 5,856,322 A | 1/1999 | Belley et al. | |
| 5,869,673 A | 2/1999 | Tung et al. | |
| 6,063,802 A | 5/2000 | Winterborn | |
| 6,320,052 B1 | 11/2001 | Bhupathy et al. | |
| 2004/0265375 A1 | 12/2004 | Platteeuw et al. | |
| 2005/0107426 A1 | 5/2005 | Overeem et al. | |
| 2005/0245568 A1 * | 11/2005 | Overeem et al. | ............. 514/311 |
| 2005/0245569 A1 * | 11/2005 | Overeem et al. | ............. 514/311 |
| 2007/0135480 A1 * | 6/2007 | Benovsky et al. | ............. 514/311 |
| 2007/0135642 A1 * | 6/2007 | Benovsky et al. | ............. 546/180 |

FOREIGN PATENT DOCUMENTS

| | | | |
|---|---|---|---|
| CN | 1420113 A | * | 5/2003 |
| EP | 0 480 717 | | 4/1992 |
| WO | WO 95/18107 | | 7/1995 |

OTHER PUBLICATIONS

March, J. Advanced Organic Chemistry 4th Ed., 1992., pp. 323, 357.*
Alfa Aesar Chemical Catalog, A Johnson Matthey Co. 2006-2007, pp. 1414.*
Carey, F.A.: Sundberg, R. J. Advanced Organic Chemistry, 4$^{th}$ Edition, Part A, Kluwer Academic/Plenum Publishers, pp. 204-215.*
"An Efficient Synthesis of LTD$_4$ Antagonist L-699,392" by A.O. King et al., *J. Org. Chem*. 1993, 58, pp. 3731-3735.
Organic Synthesis, Coll. vol. 10, p. 200 (2004); vol. 76, p. 228 (1999).

* cited by examiner

*Primary Examiner*—Rita J Desai
*Assistant Examiner*—John Mabry
(74) *Attorney, Agent, or Firm*—Mark R. Buscher

(57) ABSTRACT

The reaction of methylmagnesium halide is improved by the presence of a cerium (III) salt such as cerium trichloride. The reactions are typically associated with the production of montelukast, a pharmaceutically useful compound of the following formula and salts thereof. Further enhancements can be derived from certain intermediates, salts thereof and/or purification thereof before and/or after the reaction involving methylmagnesium halide.

19 Claims, No Drawings

PROCESS FOR MAKING MONTELUKAST AND INTERMEDIATES THEREFOR

This application claims the benefit of priority under 35 U.S.C. § 119(e) from U.S. provisional patent application Ser. No. 60/737,752, filed Nov. 18, 2005; Ser. No. 60/794,429, filed Apr. 24, 2006; and Ser. No. 60/824,382, filed Sep. 1, 2006, the entire contents of each provisional application being incorporated herein by reference.

BACKGROUND OF THE INVENTION

The present invention relates to the synthesis of montelukast, a pharmaceutical agent, as well as to intermediates and processes useful in the synthesis.

Montelukast, chemically [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropane acetic acid, has the following structure of formula (1):

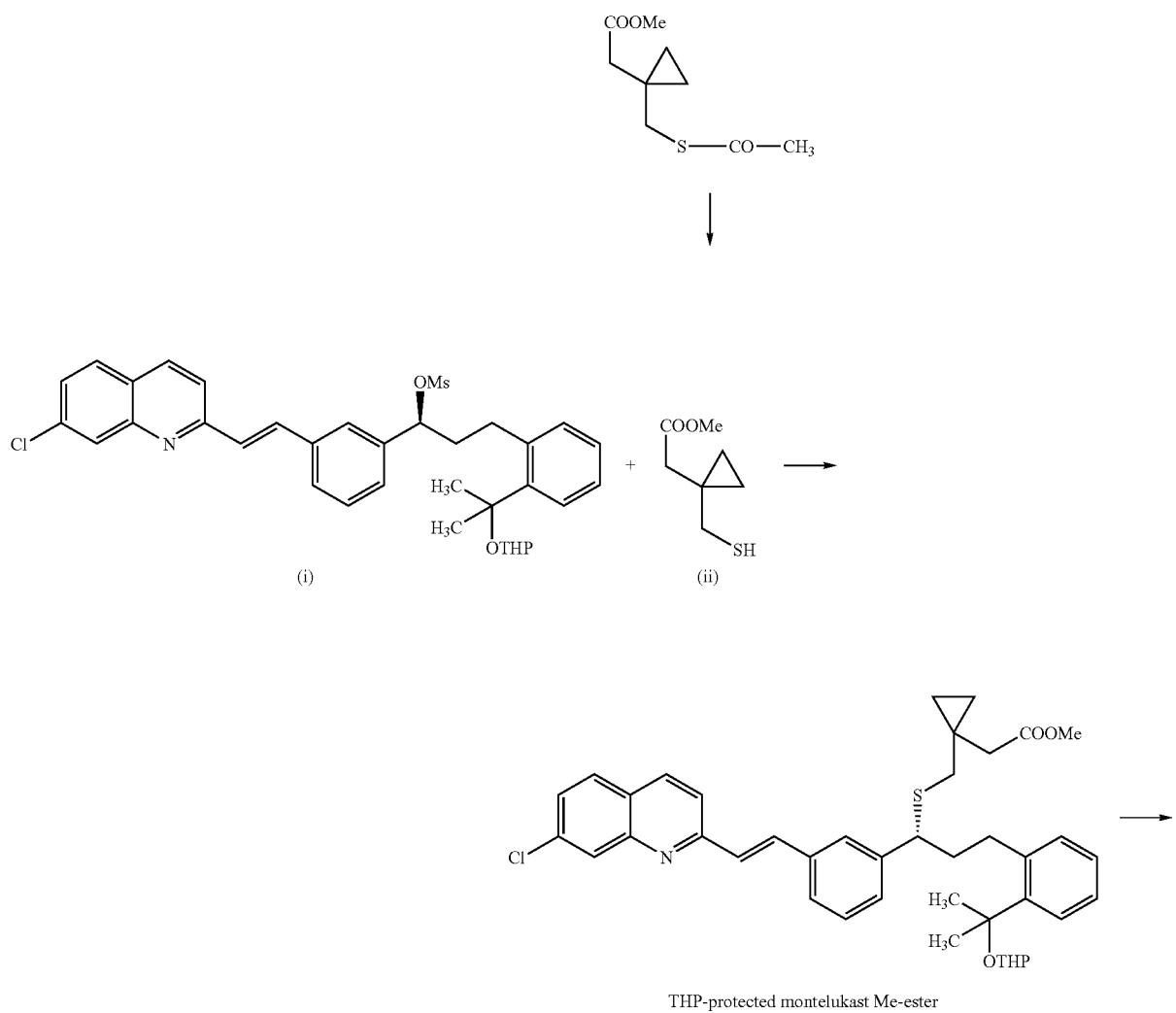

Montelukast monosodium salt (montelukast sodium) is commonly used for treatment of asthma and/or seasonal allergies. It is marketed under the brand name SINGULAIR® (Merck) in the form of oral tablets, chewable tablets, and granules.

U.S. Pat. No. 5,565,473 to Belley et al. (see also corresponding EP 0 480 717) discloses a genus of pharmaceutically useful compounds that encompasses montelukast and salts thereof. Example 161 in connection with example 146 of U.S. Pat. No. 5,565,473 disclose the synthesis of montelukast sodium as follows:

THP-protected montelukast Me-ester

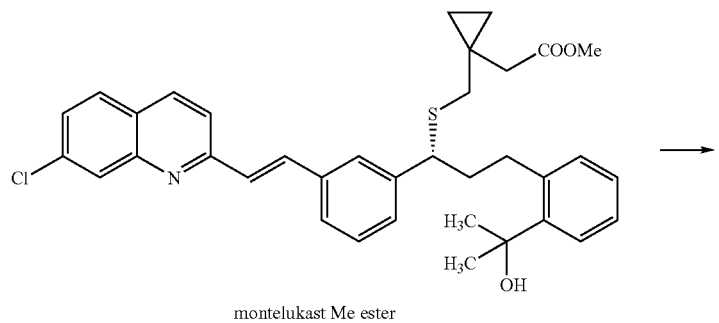

montelukast Me ester

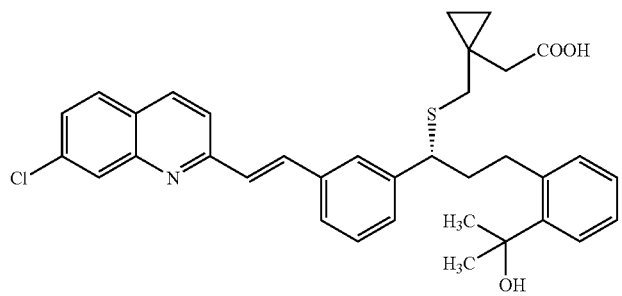

THP as used herein means tetrahydropyranyl group.

Many other synthetic schemes are proposed in U.S. Pat. No. 5,565,473 for making unsaturated hydroxyalkylquinoline acids, which may generically include montelukast. However, none of these other schemes were specifically applied to making montelukast. For example, Method B in U.S. Pat. No. 5,565,473 comprises reacting a compound of "general formula (XII)" with an organometallic compound of formula $R^2M$ to give a compound of "general formula (Ia)". Applying the corresponding substituent groups for montelukast, the method would follow the scheme below, wherein the compound of formula (2) is the representative compound of "general formula (XII)":

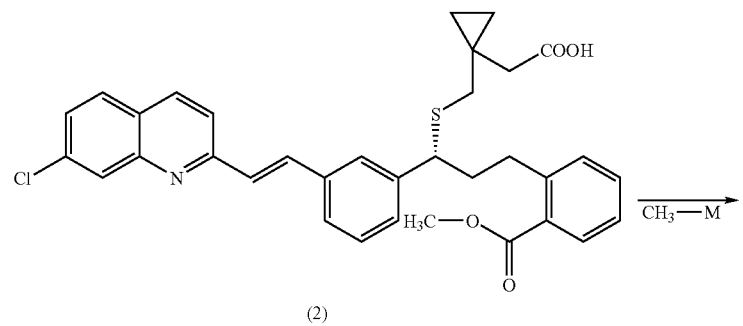

(2)

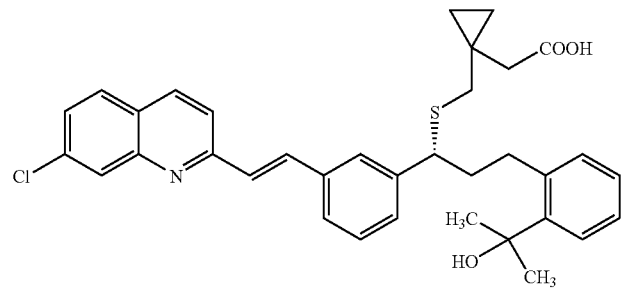

M is suggested to be MgBr or Li in Method A. The only disclosed process for making the compounds of "general formula (XII)" is not desirable for making montelukast, i.e. for making the hypothetical compound of formula (2). Specifically the process in Method B calls for a coupling reaction with a compound of "general formula (XI)." If applied to the corresponding substituents for montelukast, the reaction would be as follows:

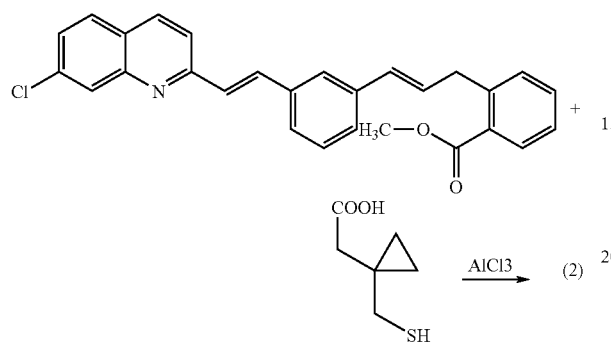

But this process cannot provide the compound (2) stereoselectively in the R-configuration as suggested above, which is required for the montelukast synthesis. Instead, only a racemic product may be obtained and no method has been suggested how to resolve the racemate into single enantiomers.

A suitable process for making montelukast starts from a methyl ester compound (18).

18

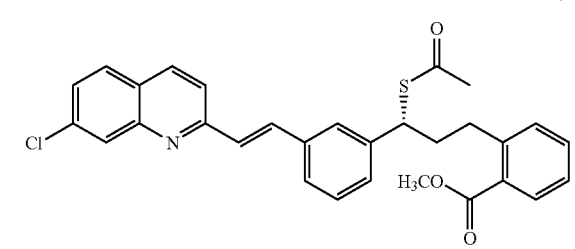

The compound (18) is a known compound of the prior art (see Compound XXVII in EP 480717) and can be produced by Steps 1-2 of the example 146 in EP 480717. It can be isolated in solid form as a monohydrate.

In an earlier patent application by some of the present inventors, Published Application No. US-2005-0245568-A1 filed Mar. 17, 2005, an acetylthio ester compound of formula (20)

(20)

was disclosed as an intermediate in a process for making montelukast and may be produced from the compound (18) as shown in the following reaction scheme:

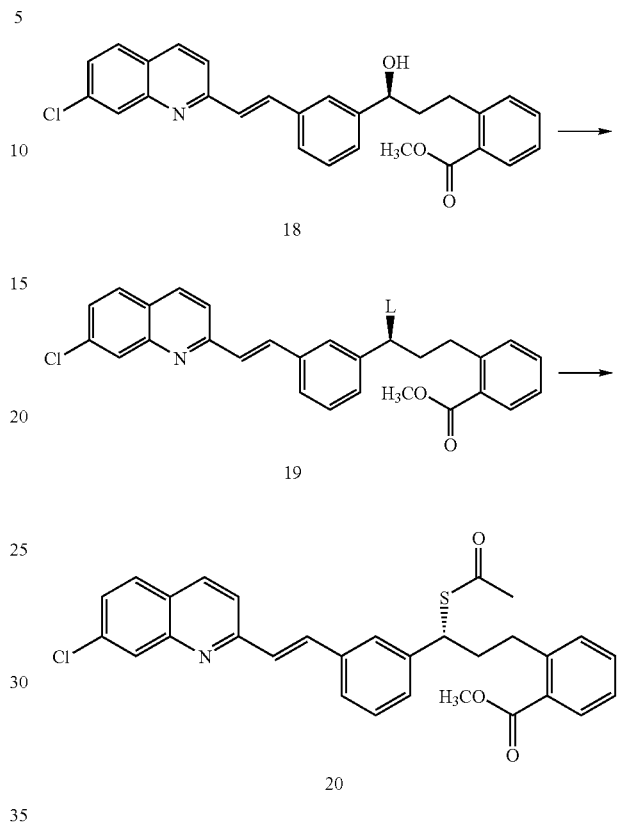

The compound (20) may be reacted, optionally after its conversion to the thiol compound (3)

(3)

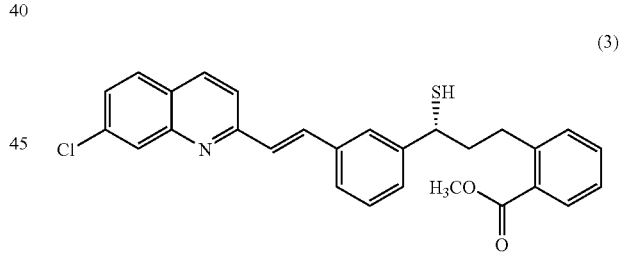

by treatment with hydrazine as described more fully in the above-mentioned US-2005-0245568, with a compound of formula (5):

(5)

wherein in the above formulas R is hydrogen or C1-C4 alkyl group, and L is a leaving group selected from a halogen or an alkyl- or aryl-sulfonyloxy group, to form a compound of formula (2) as in U.S. Pat. No. 5,565,473, or more generally (2a):

(2)

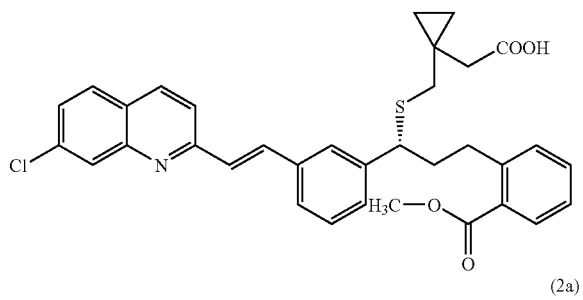

(2a)

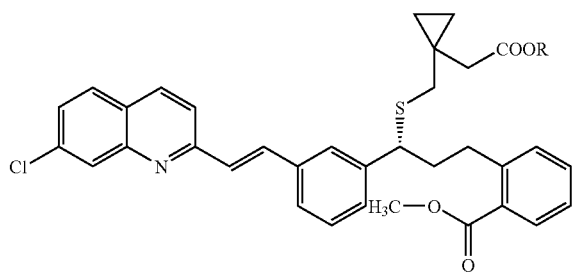

wherein R is H or a C1-C4 alkyl group. Thus, when R is hydrogen in formula (5), the compound (2) is directly formed. When R is a C1-C4 alkyl group in formula (5), then the compound of formula (2a) is formed. L is described as typically representing a chloro, bromo, mesyloxy, besyloxy or tosyloxy group. The reaction can take place in an inert solvent in the presence of a base and preferably under the atmosphere of an inert gas. The compounds of formula (2) and (2a) can be converted to montelukast or a salt thereof, generally by methylmagnesium halide, as shown in U.S. Pat. No. 5,565,473, optionally with hydrolysis.

In an alternate reaction pathway, which has been disclosed in another application filed by some of the present inventors—Published Application US-2005-0245569-A1 filed Mar. 17, 2005—the compound (20) is subjected to a reaction with methyl lithium in an inert solvent such as tetrahydrofuran, to form compound (6) as shown in the following reaction scheme:

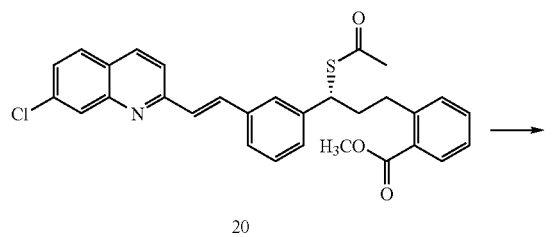

20

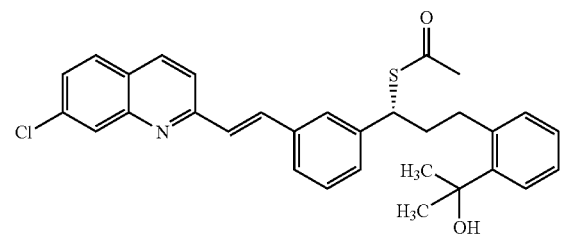

6

In a next step, the compound (4) is made in situ from the compound of formula (6) by a reaction with hydrazine and it may be subsequently converted to montelukast. The reaction scheme can be expressed as follows:

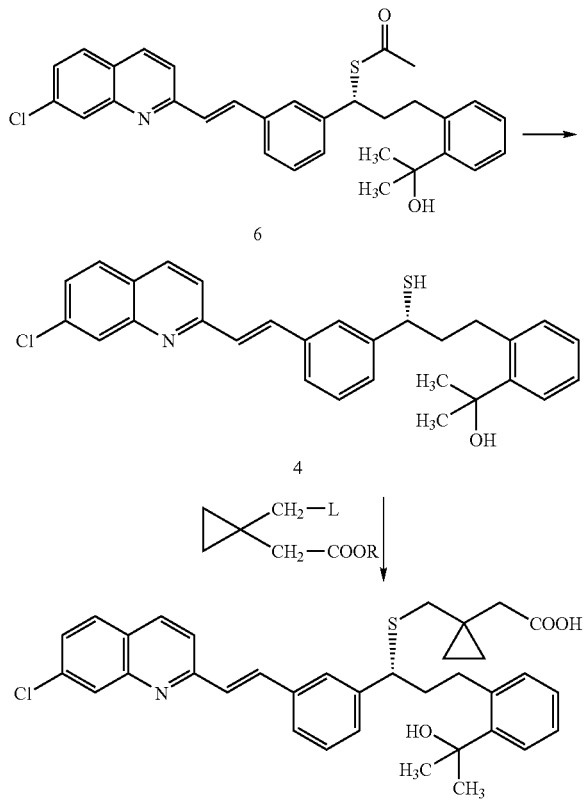

It would be desirable to provide an alternate way to make montelukast which would be suitable for a large scale production and/or to improve the above described various methods. In particular, processes that can achieve good yields and high purity and that can be reliably controlled are important in industrial pharmaceutical chemistry.

SUMMARY OF THE INVENTION

The present invention relates to the discovery of intermediates and processes associated with the synthesis of montelukast.

A first aspect of the invention relates to an acid addition salt selected from the group consisting of the compounds of formulas (4a), (4b), and (4c):

(4a)

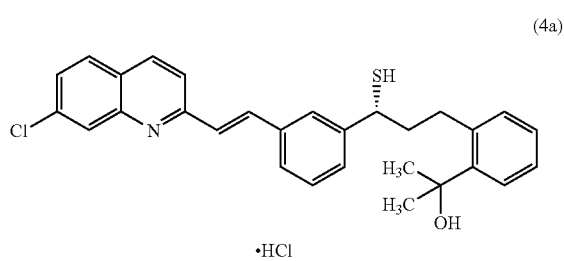

·HCl

-continued

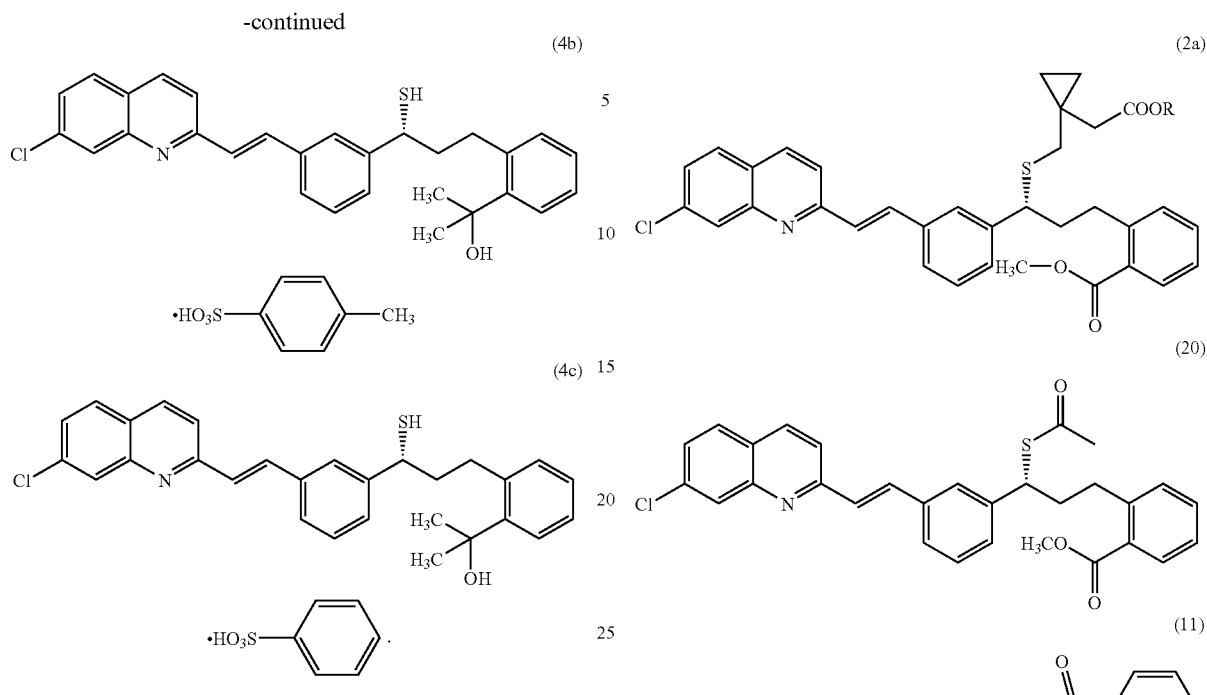

These salts are more stable than the free base and can provide a convenient way to handle, store, or purify the compound of formula (4).

Similarly, another aspect of the invention relates to an acid addition salt selected from the compounds of formulas (20a) and (20b):

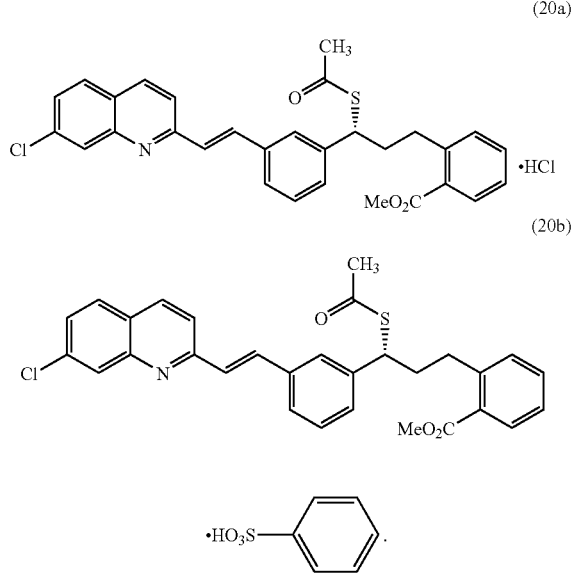

These compounds are also useful for making montelukast and/or in purifying the compound of formula (20).

A further aspect of the invention relates to a process, which comprises reacting a methylmagnesium halide with a methyl ester compound of formula (2a), (20), or (11)

or an acid addition salt thereof, wherein R represents hydrogen or a C1-C4 alkyl group, in the presence of a cerium (III) salt. The cerium (III) salt is typically cerium trichloride. The presence of the cerium (III) salt, especially in an enhanced level of activation, can reduce the level of ketone unreacted/side-product in favor of the desired alcohol.

DETAILED DESCRIPTION OF THE INVENTION

References to compounds or formulas throughout the specification include the base as well as the acid addition salts thereof, unless otherwise specified. Also, the word "isolated" as used throughout refers to separating the target compound from at least a portion of its environment so as to recover the target compound in a more concentrated form. Typically the isolation step involves a phase separation technique wherein the target compound is preferentially obtained in one phase whereby it is more easily recovered in a more concentrated form. Traditional examples of isolation techniques include precipitation and/or crystallization (e.g., solid-liquid separations), evaporating or distilling off all or a portion of the solvent(s) (e.g., vapor-liquid separations), liquid-liquid phase separations such as by extractions or decanting, etc. While isolation can and frequently does have a purification effect, it is not required that impurities per se are reduced or removed.

A useful starting material for making montelukast is the compound of formula (20), which may be obtained by a process starting from a methyl ester compound (18) as shown in the following reaction scheme:

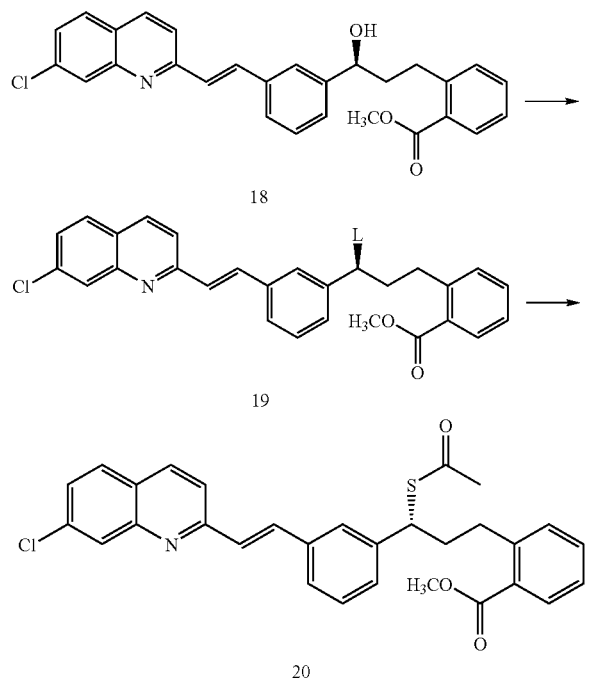

18

19

20

The compound (18) is a known compound. It can be isolated in solid form as a monohydrate. As the compound (18) is a well defined solid material, it is a very convenient starting material for the whole montelukast synthesis.

A suitable process for conversion of the compound (18) into compound (20) comprises the following sequence:

In the first step, the OH— group in (18) is first made labile by converting it into a reactive group L such as an alkyl- or aryl-sulfonyloxy group, preferably a mesyloxy group. The product is the compound of general formula (19) and the compound bearing the mesyloxy group (19a) is typically preferred.

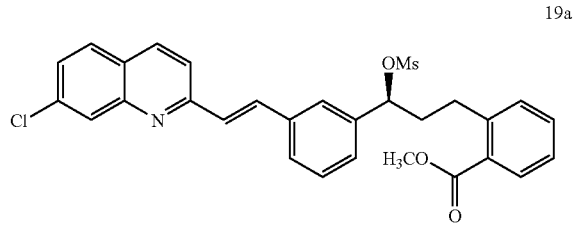

19a

The mesylation comprises contacting compound (18) with methanesulfonyl chloride in an inert solvent in the presence of a suitable base, e.g. a tertiary amine such as triethylamine.

The labile compound (19) is then converted into an acetylthio ester compound (20) by reaction with a thioacetic acid or salt thereof, for instance sodium or potassium thioacetate, in an inert solvent. If the thioacetic acid is used, a base, e.g. triethylamine, is typically also present. In this way, the labile L— group is replaced by the CH$_3$—CO—S— group. The reaction normally proceeds in a suitable inert solvent such as toluene, dimethylformamide or mixtures thereof, and generally at temperatures close to and including ambient, e.g. 0-60° C.

After conventional work-up of the reaction mixture, the compound (20) is typically isolated as a free base, which is an oil. The present inventors however found out that the base (20), albeit a very week base, may be converted into acid addition salts, some of which may be isolated as solid compounds. From this aspect, the preferred salts are the hydrochloride (20a) and the benzenesulfonate (20b),

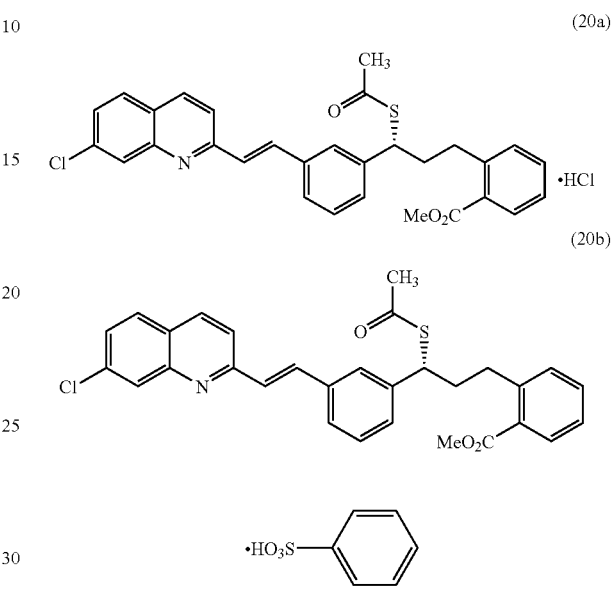

(20a)

(20b)

also suitable are the p-toluenesulfonate (20c) and the sulfate (20d). The isolation of compound (20) in a solid form is normally connected with a purification effect, as many of the side products remain in the reaction mixture. Also the optical purity of the isolated product is generally higher than when the compound (20) would be isolated as a free base.

The acid addition salts may be prepared by contacting the compound (20) with the corresponding acid in a suitable solvent, such as an C2-C8 aliphatic ketone, e.g., acetone, C2-C8 aliphatic ester, e.g., ethyl acetate, C1-C4 aliphatic alcohol, e.g. isopropanol, a C2-C6 aliphatic amide such as dimethylformamide, and mixtures thereof. The temperature of the contact may be from −20° C. to the boiling point of the solvent. The salt generally precipitates spontaneously and may be isolated at ambient temperature or at a temperature close to ambient, typically at 0-35° C. After isolation of the compound (20) as an acid addition salt, and preferably as the hydrochloride (20a), the product can have chemical purity of 99% or and optical purity of 98% or higher.

The isolated salt of the compound (20) may be converted back to the free base or used as the salt in the next reaction step. The overall advantage of these steps is that the compound (20) is isolated in a solid, stable and well processible form and the isolation of the salt brings the possibility of purification of the compound (20) before the next reaction steps. The hydrochloride (20a) and the besylate (20b) thus form a particular aspect of the present invention.

The compound (20) can then be converted into an intermediate compound of formula (6) or (2), as described in the above patents and applications, or to an intermediate compound of formula (11). The conversion to formula (11) is generally performed by reacting the compound (20) with a methylmagnesium halide, preferably methylmagnesium chloride, bromide, or iodide. Typically the reaction is carried out in an inert solvent such as toluene with 2-3 molar equivalents of an etheral solution of methylmagnesium halide. The temperature of reaction generally should not exceed 10° C. and is preferably between 0° and 5° C., though higher temperatures can be used especially later in the reaction. The reaction time is preferably from 1 to 6 hours. The course of reaction may be monitored by a suitable analytical technique, e.g. by HPLC. After the reaction is completed, the reaction mixture is worked up by treatment with water (preferably acidified water such as a diluted acetic acid), the product is preferably extracted by an organic solvent and isolated from the solvent.

The crude solid product (11), as obtained, may be further purified by any suitable technique such as through crystallization or by column chromatography, to obtain the desired degree of purity, if needed. Advantageously, the compound (11) may be purified by crystallization from a solvent comprising a mixture of a cyclic ether liquid (e.g. tetrahydrofuran or dioxan) and a second liquid selected from a C1-C4 alcohol (e.g. methanol or ethanol), C2-C6 ester (e.g. ethyl acetate), C4-C8 hydrocarbon (e.g. toluene), C3-C8 ketone (e.g. acetone) and mixtures thereof. The crystallization may be performed (i) by dissolving the compound (11) in a hot solvent mixture followed by cooling the solution, (ii) by adding the second liquid as an antisolvent to a solution of compound (11) in the cyclic ether liquid, or (iii) by a combination of these cooling and antisolvent techniques. Alternatively purification can be achieved by crystallizing the compound (11) as an acid addition salt. Generally the compound (11) is treated or combined with an organic or inorganic acid to form a salt. For example contacting with hydrochloric acid forms the hydrochloride (11a).

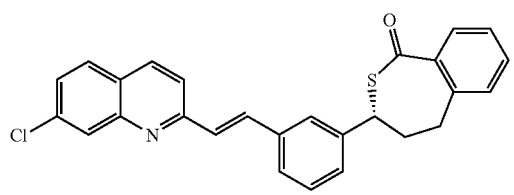

(11a)

The salt, and preferably the hydrochloride salt (11a), may be isolated in solid state from the reaction mixture, whereby most of the side products and residual reagents remain in the mother liquor. This salt may be converted back to the free base by treatment with a suitable organic or inorganic base, whereby the compound (11) is obtained in a higher degree of purity, though it is not required in order to carry out the next reaction steps.

Advantageously, the compound (11) has a chemical and/or optical-purity of at least 90% and may even exhibit 98% purity or higher.

The hydrochloride salt of the formula (11a) forms a particular aspect of the invention. The product (11), especially its salt such as (11a), may be stored at conventional storage conditions without a loss of quality, which is advantageous particularly at industrial scale.

In the next steps the compound (11) is converted to montelukast. In a typical scheme, the process goes via the intermediate of the formula (4) or a salt thereof

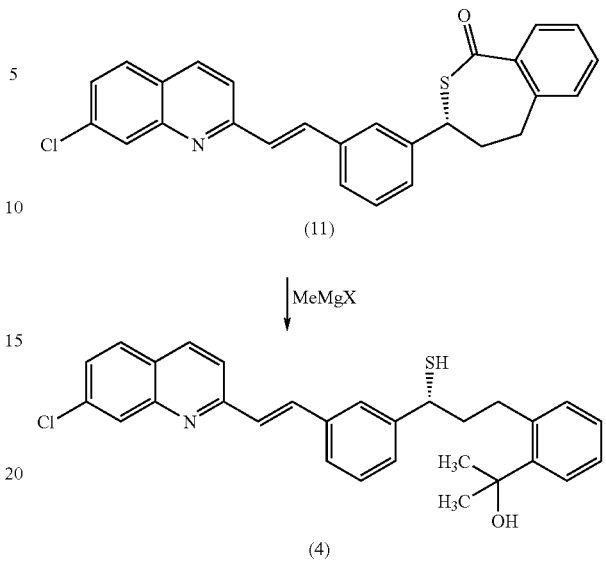

The compound (11) is treated with a methylmagnesium halide, i.e. methylmagnesium chloride, bromide or iodide, in an etheral solvent, such as in tetrahydrofuran, optionally under the presence of an inert co-solvent such as toluene, to make the compound (4). At least two molar equivalents of the methylmagnesium reagent are necessary, but advantageously 3-8 equivalents may be used. The reaction temperature is generally within the range of −15° to 15° C.

It has been found out that a serious amount of an impurity appears in this reaction step. This impurity is a ketone of the formula (12),

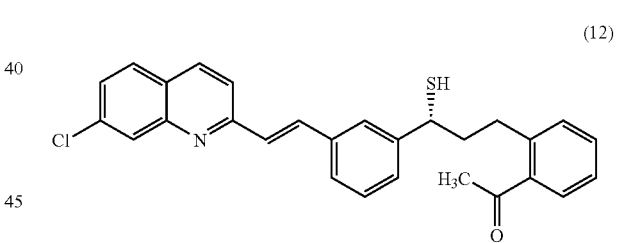

which is a natural intermediate and the primary product of the ring-opening reaction on the compound (11). One may expect that this ketone will react with the next equivalent of methylmagnesium halide to form the desired tertiary alcohol (4), but this happens only to a certain extent and 10-20% of the ketone typically remains in the reaction mixture even under a presence of large molar excess of the methylmagnesium halide and prolonged treatment. It is theorized that this is because the compound (12) is prone to enolization, which prevents the compound from further reactions. However, it has been discovered that the formation of the compound (12) in the reaction mixture may be minimized by adding a cerium (III) salt, for instance cerium trichloride, to the reaction mixture, which suppresses the enolization and therefore affords more complete conversion of the compound (12). The cerium (III) salt may advantageously be an activated cerium (III) salt. The activity of a cerium (III) salt can be enhanced by conditioning or incubating the salt with an ethereal solvent such as a cyclic ether, e.g. tetrahydrofuran, before its use. A cerium (III) salt that exhibits enhanced activity as a result of such conditioning is an "activated cerium (III) salt." Conveniently the cerium (III) salt is added in a solution or suspension of a cyclic ether, preferably tetrahydrofuran, whereby the salt and cyclic ether have been in a mutual contact for at least 4 hours, typically at least 8 hours, and in some embodiments at least 12 hours, prior to the use of the reagent. In such a way, the activity of the cerium (III) salt is substantially enhanced; allowing the use of an "activated cerium (III) salt." In the case of methylmagnesium chloride or bromide, it was observed that the presence of the activated cerium (III) salt is especially important as these two halides would otherwise provide very low conversion rates. The amount of the cerium compound is at least one molar equivalent, and advantageously 2-4 molar equivalents. By using the cerium (III) salt, and preferably the activated cerium (III) salt, the amount of the ketone compound (12) remaining in the reaction mixture may be less than 5% and even less than 1%. The course of the reaction may be monitored by a suitable analytical method, e.g. by HPLC.

After a conventional workup (a decomposition of the magnesium-comprising complex by an acidified water), a solution of the compound (4) in the inert solvent may be used immediately for the next reaction step or the inert solvent can be evaporated first. Generally, however, the compound (4) is isolated as a salt as described in more detail below.

In an alternative process, the compound (4) may also be made directly from the compound (20) without the isolation of the compound (11) by using considerable excess of the methylmagnesium halide, particularly methylmagnesium iodide. This process has been suggested in the CN 1420113A. In this process, the same problem of the ketone impurity (12) arises as it is also formed in considerable amounts (5-10%). It has been discovered that a cerium (III) salt, for instance cerium trichloride, and preferably the above defined activated cerium (III) salt, may be used for the activation of methylmagnesium halide. This way, the amount of the ketone impurity is surprisingly minimized and the process is considerably improved. In addition, methylmagnesium chloride or bromide may be used for the reaction upon such modification as it has been observed that only the methylmagnesium iodide reacts under the conditions disclosed in the CN 1420113.

The compound (4), when prepared by any of the synthetic processes described above, is not generally isolable in a solid state as the base. Therefore, the purification of it, whenever desired, is problematic. However, the compound (4) may be converted into an acid addition salt, that is crystalline. By precipitating out the crystalline salt from the reaction mixture, the overall purity of the compound (4) is improved as many of the side products, and particularly the ketone impurity, remain in the solution.

Suitable salts of the compound (4) that may be precipitated in a solid state are the hydrochloride (4a), the tosylate (4b) and the besylate (4c).

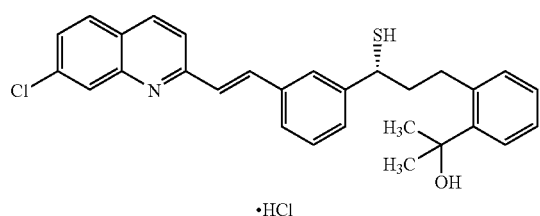

(4a)

·HCl

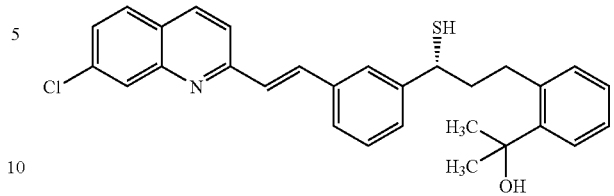

(4b)

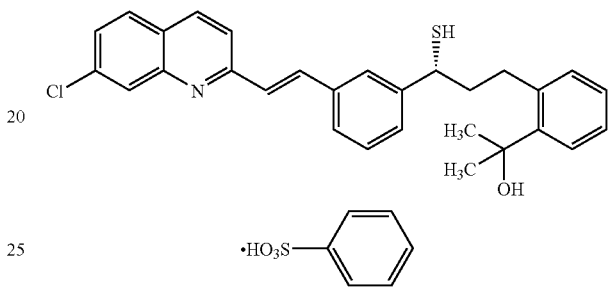

(4c)

In an advantageous mode, the salts of the compound (4) and particularly the compounds (4a), (4b) or (4c) may be prepared in the solid state by reacting the solution of the compound (4), e.g. in toluene, with the equivalent amount of the corresponding acid at ambient temperature. An antisolvent that induces or improves the precipitation (e.g. ethyl acetate) may be added subsequently for improving the process.

In an example, the original 80% purity of the compound (4) may be enhanced to 96% purity of the precipitated tosylate (4b) or besylate (4c) by this simple process. In particular, the undesired keto-impurity may be removed from the product this way.

In addition, the salts are a suitable means for storing the compound (4) for an extended time without substantive decomposition (the compound (4) is inherently very unstable compound). From this aspect, the compounds (4b) and (4c) are particularly suitable as they may be isolated as a crystalline stable material. Furthermore, the salts (4a), (4b) and (4c) may serve as analytical standards for monitoring the quality of the compound (4) and/or the course of a reaction employing the compound (4).

For further steps in the process of making montelukast, the salt may be easily converted back to the compound (4) by neutralization with a suitable base, or it can be used as the salt. In a next step, the compound (4) (as a base and/or as a salt thereof) is subjected to a reaction with a compound of formula (5).

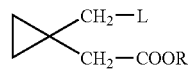

(5)

The R in the compound of formula (5) may be hydrogen or a C1-C4 alkyl group, and preferably is a methyl or ethyl group. The leaving group L may be halogen or/and alky- or arylsulfonyloxy group.

The thiol intermediate (4), if not converted to a salt, is very prone to spontaneous side reactions, particularly involving the oxidation of the thiol group into a disulfide group. Thus whenever the base (4) is used after the cleavage step, the compound of formula (5) should be added shortly thereafter in order to reduce impurities/side-products; generally within three hours and typically within one hour. Similarly, if (4) is converted to a salt and re-converted back to the base, the reaction with the compound (5) should be relatively immediate after the re-conversion. Such timing issues are less important for the salts of compound (4), which can even be stored in solid state for later use. The latter are more stable to such side reactions while still maintaining sufficient reactivity for the reaction with compound (5). In practice, if the compound (4) is used in its base form, it is dissolved/dispersed in an ethereal solvent such as tetrahydrofuran.

Typically, an alkaline hydroxide or alkoxide, such as lithium hydroxide or sodium methoxide, serves as a base in the nucleophilic substitution of the side chain of (5). The reaction normally proceeds in a solvent which is typically a solvent mixture comprising an alcohol, for instance a methanol/acetonitrile mixture or methanol/tetrahydrofuran mixture. The reaction is generally carried out under an atmosphere of an inert gas, such as nitrogen or argon. The combination of the above conditions serves to minimize the undesired side reaction of the thiol group into a disulfide group.

In the previously mentioned published patent applications, the preferred compound of the general formula (5) for making montelukast was the bromo-ester of the formula (5a).

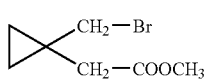

(5a)

The present inventors found out, however, that this compound undergoes a serious side reaction under the desired reaction conditions, particularly to a re-arrangement yielding a cyclobutane derivative of ring structure (5-1), often followed by the product of the ring opening of the structure (5-2).

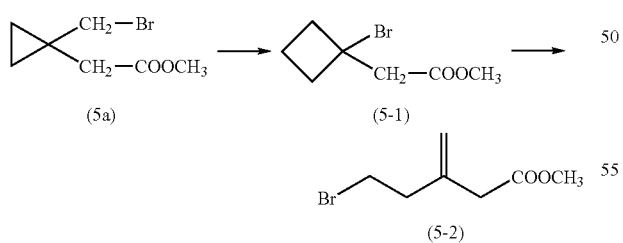

Both side products are similarly reactive as the compound (5a) itself, thus yielding a row of impurities structurally related to montelukast, which may be removed from the desired product only with difficulties.

From this aspect, the more preferable reagent for the montelukast synthesis is the p-methoxybenzene sulfonyloxy compound of formula (5b),

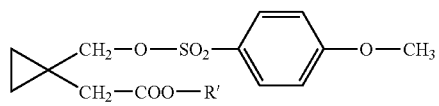

(5b)

wherein R' is a C1-C4 straight or branched alkyl group and preferably is methyl group.

The presence of p-methoxy group in the molecule provides an electron-donating effect which is sufficiently high to achieve the desired improved stability and sufficiently low that reactivity with the intended reaction partner is maintained.

The methyl ester [(5b), R=methyl] has chemical stability similar to the corresponding bromo-compound (5a), but it is more stable than, for instance, analogous methanesulfonyloxy-, p-toluenesulfonyloxy- or benzenesulfonyloxy compounds (which are so unstable that they can be isolated only with difficulties). This compound has a lower tendency to the rearrangement and ring-opening reaction shown above for the bromo-compound. And it is very well detectable in UV-light at the conventional wavelength 254 nm, which is useful for monitoring the reaction process by HPLC with UV detection. Accordingly, the compound (5b) and particularly the methyl ester, forms a specific aspect of the present invention.

The compound (5b) may be produced by any process known in the art for making of compounds of the general formula (5). In particular, it may be produced by reacting the compound of formula (15)

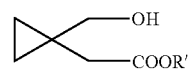

15 wherein R is a C1-C4 alkyl group, with p-methoxybenzenesulfonyl halide, particularly p-methoxybenzenesulfonylchloride in a presence of a base, preferably pyridine, according to the scheme:

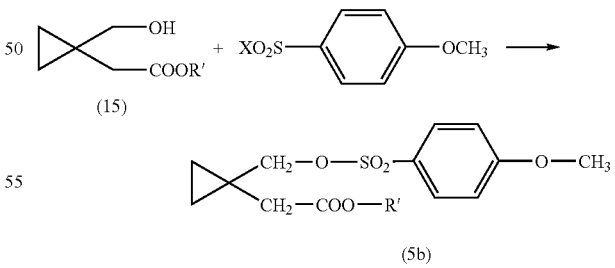

It is useful in any process for making montelukast, i.e. not only for the reaction with the compound of formula (4) as preferred within the present invention, but, e.g., also in a process using the compound of formula (20) or (3) as the reaction partner.

When the product of the reaction with compound (5) is an ester compound of formula (1a),

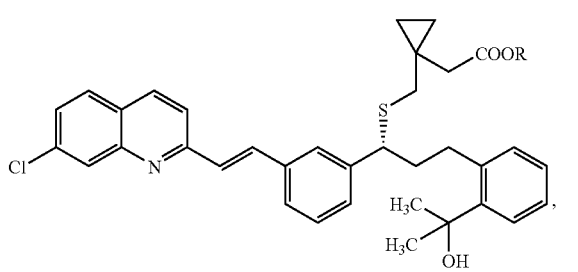

wherein R is C1-C4 alkyl group, and typically is methyl group, it is normally converted by hydrolysis to provide the desired montelukast compound (1). Preferred hydrolytic conditions comprise an alkaline hydrolysis. Advantageously, the hydrolysis occurs directly in the reaction mixture after the coupling of the compound (4) with the compound (5). To achieve this, the reaction mixture comprises at least an equimolar amount of water (which may be added or may be inherently present).

The final product of the process is montelukast acid. It may be used in pharmaceutical applications per se, for instance in a solid form, which has been disclosed in U.S. Patent Publication US-2005-0107426-A1 filed Oct. 8, 2004, entitled "Solid State Montelukast," the entire contents of which are incorporated herein by reference. Alternatively, the montelukast acid may be converted into various salts, of which the sodium salt is preferred, by known methods.

Several important observations should be included:

a) The role of cerium (III) compounds is substantive also in other processes for making montelukast, in which methylmagnesium halide is used for reductive methylation on an ester group. For instance, the conversion of the compound (2) to montelukast of formula (1) disclosed in the earlier published patent application US-2005-0245568-A1 and outlined above may suffer from the same problem of the formation of a stable keto-intermediate, which have the formula (13) and (14) respectively,

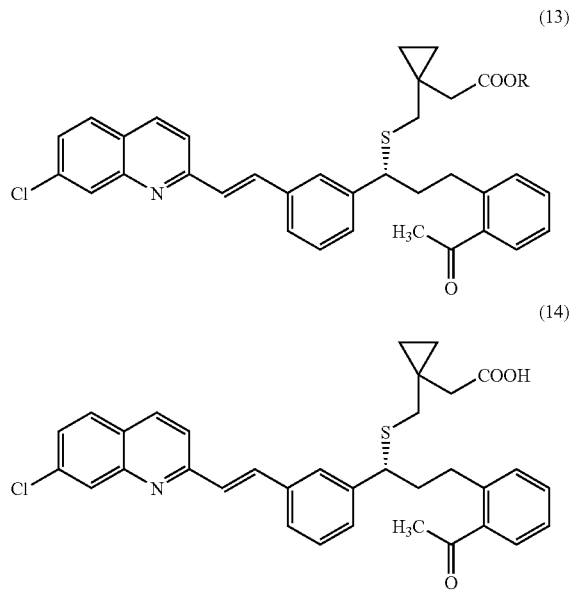

and which may form an impurity in the desired product. The addition of cerium trichloride, and preferably the activated cerium trichloride to the methylmagnesium halide is a measure that substantively minimizes the amounts of this impurity in montelukast.

b) The importance of minimizing the side products, and particularly the compound (12) in the reaction process in making montelukast according to this invention, becomes apparent from the finding that the side product of formula (12) undergoes basically the same reaction pathway as the main reagent. Thus, whenever present as an impurity in the compound (4), it also reacts with the compound (5), and the impurity of the formula (13), typically the methyl ester of the formula (13a),

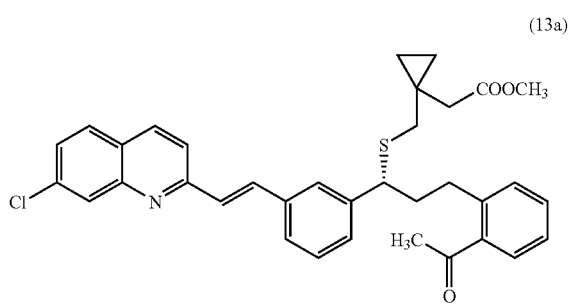

is formed. Upon saponification under conventional conditions leading to montelukast acid, it is also saponified to form an impurity of formula (14), which is very difficult to be removed from the final montelukast.

In conclusion, it should be also noted that, in essence, any production process for making montelukast, which uses a methylmagnesium halide as a reagent with an ester group, may face the problem of formation of a corresponding keto-impurity analogous to the compound of formula (12) above, and particularly the problem of formation of the compounds (13) and (14). Accordingly, such reaction process must be monitored for the presence of the compounds (12), (13) and/or (14) and appropriate measures must be made to suppress their formation. One of such measures is the addition of cerium (III) salts to methylmagnesium halide as exemplified above, but it is not excluded that also other ways may be found including purification processes. In consequence, the compounds (12), (13) and (14) are useful chemical products per se, as they may serve as reference standards in the step of monitoring the process of making montelukast, particularly when starting from the compound (20). Thus, a process of making montelukast from the compound (20) may be advantageously improved in such a way, that the relevant production step (e.g. a step using the compound (20), (11), (2) or (2a) as a substrate for the reaction with methylmagnesium halide) is monitored for the presence of the appropriate member of the group of the compounds (12),(13) and (14) and no subsequent reaction step is started unless the content of this relevant compound is below the stated limit, which could be less than 5% but preferably less than 1%. Therefore, the above described processes, with or without monitoring are capable of providing, and preferably do provide, a montelukast having the content of any of the impurities (12), (13) and/or (14) lower than 1%, and/or having a chromatographic purity higher than 99%. Such a high purity is advantageous in the production of a pharmaceutical.

In as much as several aspects of the present invention can be used in other related syntheses of montelukast, which do not involve the thiolactone compound of formula (11), the following flow chart illustrates the wide applicability of, e.g.

the use of cerium salts, the use of compound (5b), the purification of compound (20), the monitoring of certain kinds of impurities, etc., to various synthesis schemes, all of which are considered part of the invention.

cally, the montelukast acid is purified before its conversion to the sodium salt. The purification at this stage is easier and more effective than it would be if performed with the final montelukast sodium. It is known that the montelukast acid

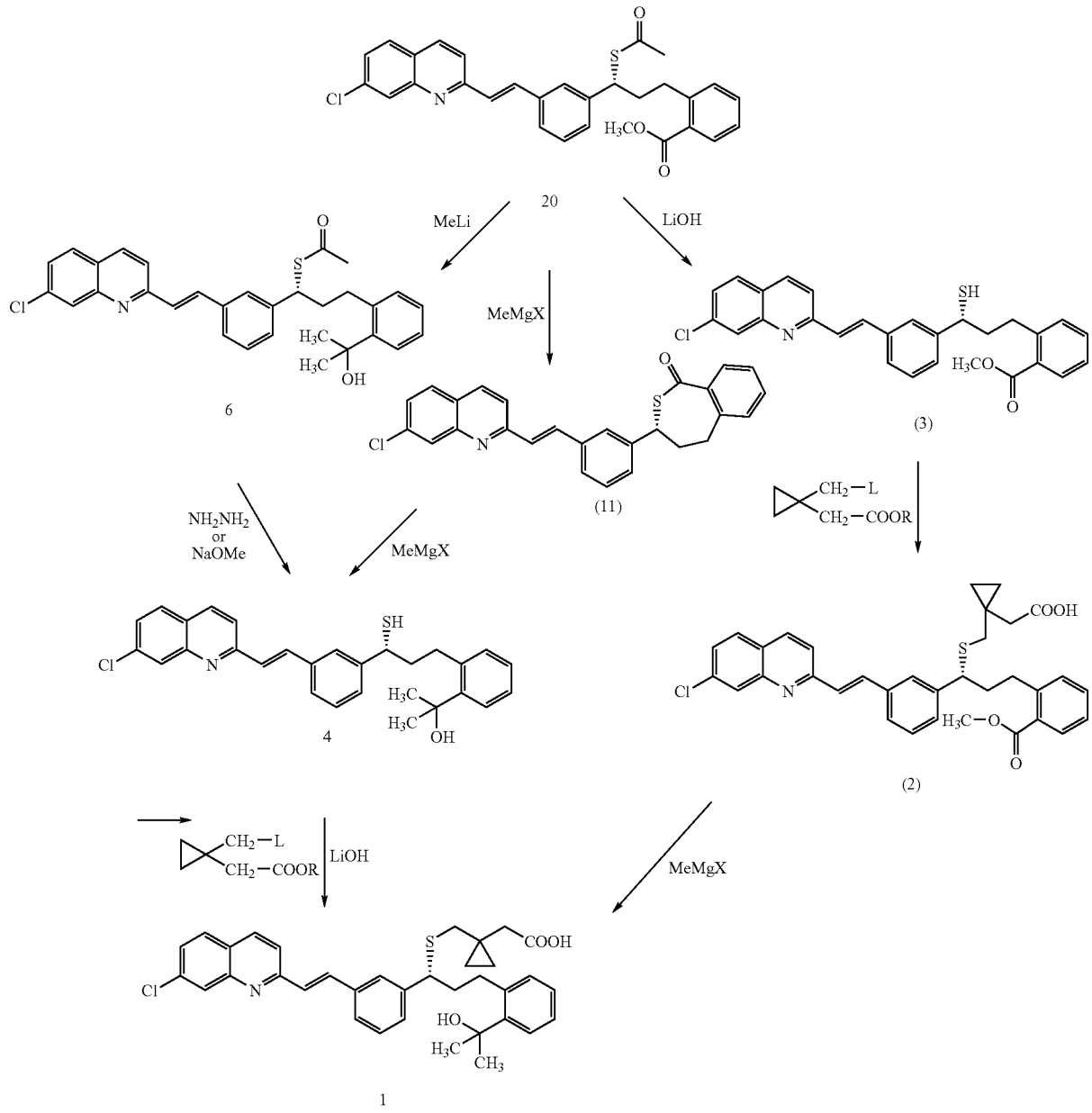

It should be understood that the reagents shown are not compulsory and not all steps or conditions are illustrated; e.g., the hydrolysis step of an ester compound to an acid compound may optionally be performed among other steps not explicitly shown. Further, while all compounds are derived in the scheme from compound (20), in practice, many of the intermediate compounds such as compound (4) and (2) can be made from other starting materials such as by the methods generally taught in Belley et al.

Once the montelukast is formed, it is often desirable to purify it to, e.g., pharmaceutically acceptable quality. Typimay be converted into a salt with dicyclohexyl amine, or with 1-amino adamantane as shown in U.S. provisional patent application Ser. No. 60/783,027, filed Mar. 17, 2006, whereby such conversions exhibit a purification effect. However, it has been discovered that it is possible to purify the crude montelukast acid effectively without a conversion thereof into a salt. The improved process comprises at least one of the following steps:

i) Filtration of the toluene solution of montelukast acid through a polar sorbent, such as silica gel, optionally followed by precipitation; and ii) Crystallization from a protic solvent such as ethanol under the absence of light.

The toluene is an advantageous solvent for the crystallization, as, on the contrary to many other solvents, substantially no trans-cis isomerisation on the double bond occurs. The polar sorbent effectively removes the oxidation products, which are particularly formed when the unstable intermediate (4) is used within the synthetic process. The alcoholic solvent effectively removes side products from the condensation of the compound (4) and (5), particularly products formed by rearrangement of the cyclopropane ring. The absence of light minimizes the trans-cis isomerisation.

Advantageously, both of the steps are performed in the purification process. The steps, when using more than one, can be employed in any order and any step may be repeated one or more times. By this, the montelukast of a purity of more than 99%, and even more than 99.5%, can be obtained.

The montelukast can be converted into montelukast salt, such as the sodium salt, by known techniques. A useful solid state form for the salt montelukast sodium is the amorphous form. It can be made by contacting montelukast sodium with an aliphatic $C_5$-$C_{10}$ straight or branched hydrocarbon solvent such as petroleum ether, hexane, heptane and mixtures thereof, and precipitating amorphous montelukast sodium. The n-heptane is generally the preferred solvent. Normally the solvent is stirred during, (at least), the contacting with the montelukast sodium. In an advantageous mode, montelukast acid is converted into the montelukast sodium by contacting thereof with sodium hydroxide or alkoxide in an organic water miscible solvent, followed by removal of the solvent, and the concentrate (which is typically a liquid or an oil) is slowly added into the stirred hydrocarbon liquid, whereby the amorphous montelukast sodium precipitates. The temperature of the precipitation is advantageously ambient temperature.

The invention is further described by way of the following non-limiting examples.

Throughout the whole description and unless stated to the contrary, the double bond attached to the 7-chloro-2-quinolinyl ring has, in all the formulas, the two non-hydrogen substituents in the same configuration as that in montelukast.

EXAMPLE 1

Compound (11)

Step 1—Compound (20)

500 g of Methyl 2-((3S)-3-[2-(7-chloro-2-quinolinyl)-ethenyl]-phenyl)-3hydroxypropyl)-benzoate monohydrate [Compound (18)] were placed into reactor and 3000 ml of toluene were added. The mixture of toluene/water was azeotropically distilled off (800 ml). Then the toluene solution was cooled to room temperature. The solution contained 480.11 g of anhydrous (18).

To the solution, 227.0 ml of triethylamine were added at room temperature and 110.2 ml of methanesulfonyl chloride were added dropwise so that reaction temperature did not exceed 40° C. Reaction mixture was subsequently stirred at 25-30° C. for 1 hour. Then 605 ml of triethylamine were added to the reaction mixture followed by addition of 156 ml of thioacetic acid at room temperature within 5 minutes. The reaction mixture was subsequently heated to 40-45° C. for 3.5 hours. 1000 ml of water were added to the reaction mixture and it was stirred for 15 minutes. The layers were separated, organic layer was subsequently washed with 2×1000 ml of brine and most of toluene was distilled off by vacuum distillation. The resulting solution was filtered and the residual toluene evaporated to dryness on the rotary evaporator giving orange-brown oily residue of crude compound (20).

Yield: 588 g (104.3%)

Step 2—Compound (11)

Work under Argon.

24.40 g of the compound (20) (crude from Example 1) were dissolved in 260 ml of anhydrous toluene (distilled from benzophenone/Na). Solution was cooled to 0-5° C. (ice/water bath). 41 ml of MeMgI in diethyl ether were added dropwise to the solution so that temperature did not exceed 5° C. (over 20 minutes). Reaction mixture was stirred and cooled to 0-5° C. Reaction was monitored by HPLC. Reaction was stopped after 4.5 h and 200 ml of water were slowly added with external cooling. Reaction mixture was subsequently acidified with 12 ml of glacial acetic acid. Layers were separated and water layer was extracted with 100 ml of toluene. Organic extracts were combined and dried over magnesium sulfate. Mixture was filtered and solvent was evaporated to dryness (bath heated to 45° C.) giving 25.52 g of crude compound (11).

$^1$H NMR (Solvent :$CDCl_3$, Field [MHz]: 400)

| Proton shift (ppm) | Multiplicity | J-coupling [Hz] | Number of protons |
|---|---|---|---|
| 2.28-2.41 | m | | 1 |
| 2.45-2.57 | m | | 1 |
| 2.91-3.01 | m | | 1 |
| 3.27-3.39 | m | | 1 |
| 4.08 | dd | 8.0; 12.0 | 1 |
| 7.17-7.73 | m | | 13 |
| 8.00-8.10 | m | | 2 |

EXAMPLE 2

Compound (11)

Work under Argon.

24.50 g of compound (20) were dissolved in 180 ml of anhydrous toluene (distilled from benzophenone/Na). Solution was cooled to 0-5° C. (dry ice/water bath). 41 ml of 3M MeMgCl in THF were added dropwise to the solution so that temperature did not exceed 5° C. (over 30 minutes). Reaction mixture was stirred and cooled to 0-5° C. No precipitation observed. Reaction was monitored by HPLC. Reaction mixture is turning cloudy—slight precipitation. Reaction was stopped after 3 h and 100 ml of water were slowly added with external cooling. Reaction mixture was subsequently acidified with 3 ml of glacial acetic acid to pH=4-5. Layers were separated and organic extract was dried over anhydrous magnesium sulfate. Mixture was filtered and solvent was evaporated to dryness (bath heated to 45° C.) giving 20.05 g of crude thiolactone (11) base.

HPLC—after evaporation—80.69%

EXAMPLE 3

Compound (11a)

2.586 g of thiolactone (11) were dissolved in 18 ml of toluene at 40° C. Solution was cooled to room temperature and 7.1 ml of 1 M aqueous HCl were added with stirring. Mixture was stirred for 2 h at room temperature. Precipitated solid material was separated by suction and washed with 5 ml of toluene and dried at room temperature.

HPLC: 95.43%

Yield: 1.43 g (63%)

EXAMPLE 4

Compound (11a)

2.182 g of thiolactone (11) was dissolved in 15 ml of toluene at 40° C. Solution was cooled to room temperature and 10 ml of 1M aqueous HCl were added with stirring. Thick precipitation has appeared so mixture was diluted with 5 ml of toluene. Mixture was stirred for 2 h at room temperature. Precipitated solid material was separated by suction and washed with 5 ml of toluene and dried at room temperature.

HPLC: 87.56%

Yield: 1.48 g (77.26%)

EXAMPLE 5

Compound (11)

9.6 ml of 5% aqueous solution of $NaHCO_3$ were placed to 25 ml flask and 10 ml of toluene were added. Mixture was stirred and 1.43 g of compound (11a) was added in portions. Suspension was heated to 40° C. (oil bath heated to 42° C.) for 1.5 h (all solid material was completely dissolved). Layers were separated and water layer was extracted with 5 ml of toluene. Toluene extracts were combined and dried over anhydrous sodium sulfate. Mixture was filtered and solvent was evaporated to dryness (bath heated to 45° C.) giving foamy brownish solid material.

Yield: 0.132 g (89.90%)

HPLC: 91.93%

EXAMPLE 6

Compound (4)

Work under Argon Atmosphere 0.450 g of powdered anhydrous cerium (III) chloride were mixed with 1.44 ml of anhydrous THF and mixture was stirred at room temperature for 16 hours. Mixture was subsequently cooled to 0° C. and 0.96 ml of MeMgCl (3M THF solution) was added dropwise (over 5 minutes). Mixture was stirred for 2.5 h at 0° C. In the mean time 0.234 g of thiolactone (11) was mixed with 7 ml of anhydrous toluene and mixture was heated to 60° C. until all solid material was dissolved. Solution was cooled to room temperature and subsequently added dropwise (over 5 min) to the mixture of organometallic reagent at 0° C. Reaction mixture was stirred and cooled to 0° C. Reaction progress was monitored by HPLC:

after 50 min: $R_T$=13.12 min–94.54%

Reaction was stopped after 1 h and it was quenched with 2.5 ml of 1M aqueous HCl to pH=4-5 with external cooling. Color turned from orange to light yellow. Mixture was stirred for 15 minutes at room temperature and layers were allowed to separate. Water layer was extracted with 2×10 ml of ethyl acetate. Organic extracts were combined and washed with 10 ml of brine and with 10 ml of saturated sodium hydrogen carbonate solution. Organic layer was subsequently dried with sodium sulfate. Mixture was filtered and solvents were evaporated on the rotary evaporator (bath heated to 45° C.) giving partially crystalline yellow residue.

Yield: 0.23 g (93%) of crude material

EXAMPLE 7

Compound (11a)

Step 1

The compound (20) (254.3 g) was dissolved in anhydrous toluene (1870 ml). Solution was cooled to 0-5° C. 3M solution of MeMgCl in tetrahydrofuran (420 ml) was added dropwise via dropping funnel to the solution of the compound (20) so that temperature did not exceed 5° C. (over 40 minutes). Reaction mixture was stirred and cooled to 0-5° C. Reaction was monitored by HPLC.

Reaction was stopped after 3 h and glacial acetic acid (72 ml) was slowly added to the reaction mixture with external cooling (foaming). Cooling was interrupted and the reaction mixture was stirred for 10 min. It was subsequently diluted with water (500 ml) and resulting mixture was stirred for 15 minutes at room temperature. Layers were separated and organic extract was stored in the dark flask. It was used in the following step without further purification or isolation.

Step 2

Concentrated HCl (54 ml) was slowly added to the solution of thiolactone base prepared in the Step 1. Mixture was stirred for 1.5 h at room temperature and then stirred at 0-5° C. for another 1 h. Precipitated solid material was separated by suction and filter cake was washed with toluene (2×150 ml). Solid thiolactone hydrochloride was dried at room temperature.

EXAMPLE 8

Compound (4)

Work under Argon and in a Dried Glass Equipment.

2.15 g of powdered anhydrous cerium trichloride was suspended in 6.90 ml of dry tetrahydrofuran and the mixture was stirred at laboratory temperature for 19 hours. The white suspension was cooled down to 0° C. and 2.91 ml of 3M solution of methylmagnesium chloride (4.5 eq.) in tetrahydrofuran was added dropwise. he mixture was stirred at 0° C. for 1.5 hours and 1.00 g of the compound (20) (purity 87%, 1.938 mmol) in 14.60 ml of dry toluene was added dropwise in the course of 20 minutes. The mixture was stirred at 0° C. for 265 minutes and then left in refrigerator (8° C.) overnight (19 hours). As the reaction was found incomplete by HPLC, 1.94 mg of 3M solution of methylmagnesium chloride (3 eq.) in tetrahydrofuran was added dropwise. The mixture was stirred at 8° C. for next 2.5 hours.

To the reaction mixture, 15 ml of water was added at 8° C. and the mixture was stirred for 15 minutes. The pH value was adjusted by glacial acetic acid to 4-5 (approx. 4 ml), the mixture was filtered, the layers of the filtrate were separated and the aqueous layer was extracted with 10 ml of toluene. Combined organic layers were dried over anhydrous sodium sulfate and filtered.

Finally the toluene solution was concentrated.

Yield: 1.10 g

EXAMPLE 9

Compound (4b)

The toluene solution of the compound (4) was prepared according to the example 8, starting with 8.5 mmol of the compound (20).

To the solution (approx. 100 ml), p-toluene sulfonic acid monohydrate (1.5 g) was added in several portions at room temperature and under stirring. The mixture was stirred at room temperature for 1 hour. 25 ml of ethyl acetate was added and the mixture was stirred for next 20 minutes.

The solid was collected by filtration and washed with 10 ml of ethyl acetate.

Yield: 2.75 g, 96% purity.

EXAMPLE 10

Montelukast (Compound (1))

1.00 g of the tosylate (4b) was suspended in the mixture of 5.00 ml of anhydrous tetrahydrofuran and 13.00 ml of methanol. Then, 0.42 g of the compound (5a) was added. To the stirred mixture, a solution of 0.251 g of sodium methoxide in 3.0 ml of methanol was added dropwise in the course of 40 minutes at 20° C. The mixture was stirred at laboratory temperature for 21.5 hours. Then, 0.31 g of sodium hydroxide in 1.5 ml of water was added at once and the mixture was heated at 55° C. for 105 minutes. Then 10 ml of toluene was added and volatile solvents (methanol, tetrahydrofuran) were removed on a rotary vacuum evaporator (50° C.). 6 ml of water was added and the pH value was adjusted with 0.5 ml of glacial acetic acid to 5. The mixture was stirred for 15 minutes and then allowed to stand for separation of layers. The aqueous layer was extracted with 2×10 ml of toluene under argon.

Combined organic layers were concentrated, 5 ml of dichloromethane was added and concentrated again. The residue was mixed with 10 ml of toluene, heated to 35° C., seeded with a crystal of montelukast and kept at this temperature for 20 hours. The mixture was filtered after cooling to 20° C., the solid washed with 2×2 ml of toluene. Solid crystalline product was dried at 20° C. protected from light.

Yield: 0.47 g. Purity (HPLC) 96.93%. Content of the ketone compound (14) 0.03%.

EXAMPLE 11

Compound (4)

98 g of anhydrous cerium (111) chloride was mixed with 370 ml of anhydrous tetrahydrofurane and the mixture was stirred at 20-25° C. for 13 hours. The mixture was then cooled to 0-5° C. and 132 ml of 3M solution of methylmagnesium chloride in tetrahydrofurane was added dropwise in 5 minutes. The mixture was stirred for 2.5 hours at 0-5° C.

Separately, 50.5 g of compound (11) was placed into a 2 l flask and dissolved in 550 ml of anhydrous tetrahydrofuran under stirring at 20-25° C. The solution was then cooled to −10 to −15° C. and the prepared pre-cooled mixture of cerium chloride/methylmagnesium chloride was added to the solution of compound (4) over 3 minutes at −10 to −15° C. The mixture was stirred at the same temperature under HPLC control and the reaction was stopped after 50 minutes. A solution of 36 ml of glacial acetic acid in 250 ml of water was slowly added to the reaction mixture at −5 to 0° C. in 2 minutes and the mixture was stirred for 15 minutes at room temperature. Layers were separated and the aqueous layer was washed with 100 ml of tetrahydrofuran. Combined organic extracts were washed with 3×100 ml of saturated aqueous NaHCO3 and with 200 ml of brine, dried by magnesium sulfate and filtered giving 950 ml of the solution of compound (4) in tetrahydrofurane. Purity: 96.00% (HPLC, IN)

EXAMPLE 12

Solid State Acid Addition Salts of (20)

a) Compound (20a)

152 g of compound (20) was mixed with 457 g of ethyl acetate and the mixture was heated to 65-70° C. Gaseous HCl (at least one molar equivalent) was bubbled through the stirred solution (NB. alternately, saturated solution of HCl in ethyl acetate, ethanol or isopropanol may be used as well). The resulting suspension was cooled to 0-5° C. and stirred for 2 hours. The formed crystals were separated by filtration and washed by cold ethyl acetate. Crystals were dried at 60° C. under reduced pressure for 12 hours. Yield: 153 g of yellow crystals, m.p. 168° C.

b) Compound (20b)

15.6 g of compound (20) and 24 g of acetone were heated under stirring to 30-40° C. 5.3 g of benzenesulfonic acid was added to the solution. After approx. 3 minutes, crystals started to separate. The suspension was cooled to 25° C. and stirred for 30 minutes. The solid product were separated by filtration and washed with cooled acetone. Crystals were dried at 60° C. under reduced pressure for 12 hours. Yield: 9 g of yellow crystals, m.p. 96-97° C.

c) Compound (20c)

17.9 g of compound (20) was suspended in a mixture of 16 g acetone and 47 g isopropanol and the mixture was heated under stirring to 60° C. 7.3 g of p-toluenesulfonic acid monohydrate was added, the resulting mixture was cooled to 25° C. and stirred for 8 hours. Crystals were separated by filtration and washed with 20 g of cooled isopropanol. Crystals were dried at 60° C. under reduced pressure for 12 hours. Yield: 12.4 g of yellow crystals, m.p. 78.5° C.

d) Compound (20d)

17.2 g of compound (20) was mixed with 120 g of acetone and, under stirring, 3.7 g of 98% sulfuric acid was added slowly. The mixture was cooled to 25° C. The solid product was separated by filtration and washed with 20 g of cooled acetone. Crystals were dried at 60° C. under reduced pressure for 12 hours. Yield: 4.1 g of yellow crystals, m.p. 90° C.

EXAMPLE 13

Compound (5b) [R=methyl]

Work under Argon.

14.71 g of compound (15) [R=methyl] was dissolved in 41 ml of anhydrous pyridine. The mixture was cooled to 0° C. and 25.05 g of p-methoxybenzenesulfonyl chloride was added portionwise within 7 minutes so that the temperature did not exceed 7° C. The mixture was stirred for 6 hours at 0° C. Conversion was monitored by TLC (silica gel 60 F254 Merck, 10% acetone in toluene (v/v), UV 254 nm). The mixture was diluted with 100 ml of dichloromethane at −10° C., 34.2 ml of concentrated HCl was slowly added in such a way that the temperature did not exceed 0° C. and the formed two layers were allowed to separate. The aqueous layer (pH<1) was extracted with 50 ml of dichloromethane and combined organic layers were washed with 50 ml of water, 50 ml of saturated aqueous NaHCO3 and 50 ml of brine. The organic layer was dried by MgSO4 and volatiles were evaporated at 35° C. and 20 torr. Yield: 34.12 g of pale yellow oil.

EXAMPLE 14

Montelukast (1)

1.89 g of the compound (5b) was dissolved in 15 ml of toluene and the solution was cooled to 5° C. Then, 3.5 ml of 24% methanolic solution of sodium methoxide was added. At the same temperature, a solution of 2.37 g of compound (4) in 44 ml of tetrahydrofuran was added dropwise during 6 minutes. The mixture was stirred at 10° C. for 23 hours under HPLC control.

Mixture was cooled to 0° C. Then a solution of 1.44 ml of acetic acid in 25 ml of 5% aqueous NaCl was added in such a way that the temperature did not exceed 2° C. Clear aqueous layer was separated and the organic layer was washed with 4×20 ml of an aqueous solution containing 2% NaHCO3 and 5% NaCl and then with 20 ml of brine. The organic layer was then dried over MgSO4, filtered and the volatiles evaporated at 45° C. at reduced pressure. The obtained yellow oil was dissolved in 3 ml of hot toluene and the mixture was stirred at room temperature overnight. Solid precipitate was filtered off and dried yielding 2.48 g of a pale yellow solid.

EXAMPLE 15

Purification of Montelukast 19.7 g of montelukast (purity 93.2%) was dissolved in 180 ml of toluene at 96° C. and the solution was cooled to 65° C. 2.0 g of silica gel (Merck, $SiO_2$ 60, 40-63 microns, 230-400 mesh) was added and the mixture was stirred for 10 minutes. Silica gel was filtered off and washed with 20 ml of hot toluene (65° C.). The filtrate was gradually cooled down to 28° C., precipitated solid product was filtered and washed with 2×5 ml of cold toluene. Yield: 16.39 g of pre-purified montelukast, purity (HPLC, IN) 97.54% optical purity (HPLC, chiral column) 99.5%.

16.10 g of the pre-purified montelukast was dissolved in 160 ml of toluene at 100° C. and the mixture was gradually cooled down to 25° C. The solid product was filtered off and washed with 2×5 ml of cold toluene. Yield: 15.43 g of purified montelukast, purity (HPLC, IN) 98.24%.

15.20 g of the purified montelukast was dissolved in 77 ml of absolute ethanol under absence of light at 80° C. (bath temperature) and the mixture was cooled to 25° C. The solid product was filtered off and washed with 2×5 ml of cold ethanol. Yield: 12.97 g of pure montelukast, purity (HPLC, IN) 99.0%, optical purity 99.65%

EXAMPLE 16

Montelukast Sodium Amorphous 2.0 g of Montelukast was dissolved in 5 ml of a toluene-methanol mixture (4:1 v/v) at 50° C. The turbid solution was cooled under stirring to 25° C. At this temperature, 0.33 ml of aqueous NaOH solution (0.15 g, 3.75 mmol) was added dropwise within 20 minutes. The solution was maintained at this temperature for 30 minutes, 0.05 g of activated charcoal was added and the suspension was filtered through Celite filter. The Celite was washed with 2×2 ml of toluene. The combined solution was evaporated almost to dryness under reduced pressure at bath temperature 38° C. Yellow viscous oil was obtained.

The oil was added dropwise into 10 ml of stirred n-heptane and stirred for 15 minutes at 25° C. White precipitate was formed. Then the mixture was stirred at 25° C. for next 17 hours. The precipitate was filtered by suction, washed with 2×10 ml of n-heptane and dried at room temperature protected from light.

Yield 1.85 g of white amorphous solid.

EXAMPLE 17

Preparation and Purification of Compound (11)

3.10 kg of the compound (20a) (purity 95%) were dissolved in 31 L of anhydrous toluene. Solution was cooled to 0° C. and 5.84 L of 3M MeMgCl in THF were added dropwise to the solution so that temperature did not exceed 5° C. during 60 to 75 minutes. Temperature was raised to 15° C. and Reaction mixture was stirred at 15° C. for 3 hours. Then 18 L of water were slowly added. Aqueous layer was discharged and reaction mixture was subsequently acidified with 1.50 kg of glacial acetic acid in 13.0 kg of water to pH=4-5. Layers were separated and the organic extract was extracted with saturated aqueous sodium bicarbonate and then partially concentrated to about one half at reduced pressure (35° C.). Concentrated solution was warmed to 85° C., 3.0 kg of ethyl acetate and 2.0 kg of ethanol was added and the refluxed mixture was cooled down to 0° C. Solid product was filtered off giving 1.6 kg of crude thiolactone (11) base (HPLC purity >95%).

The thiolactone base was dissolved in 7.5 kg of tetrahydrofurane at 60° C., methanol (7.5 kg) was added under stirring in 30 minutes and the solution was slowly cooled to 0 C. The precipitated solid was filtered and washed with 500 g of methanol. Yield 1.56 kg of the compound (11) with a HPLC purity >99%.

Each of the patents, patent applications, and journal articles mentioned above are incorporated herein by reference The invention having been thus described, it will be obvious to the worker skilled in the art that the same may be varied in many ways without departing from the spirit of the invention and all such modifications are included within the scope of the present invention as set forth in the following claims.

What is claimed is:

1. A process of chemical synthesis, which comprises reacting a methylmagnesium halide with a compound of formula (20) or (11)

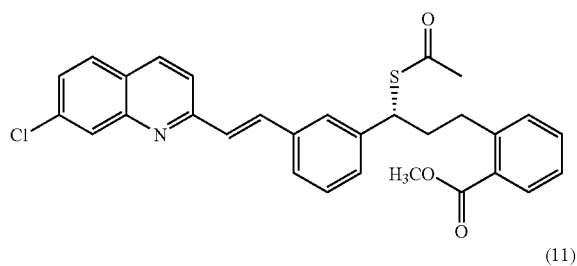

(20)

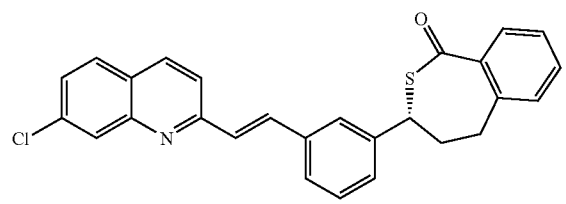

(11)

or an acid addition salt thereof, in the presence of a cerium (III) salt to produce a compound of formula (4):

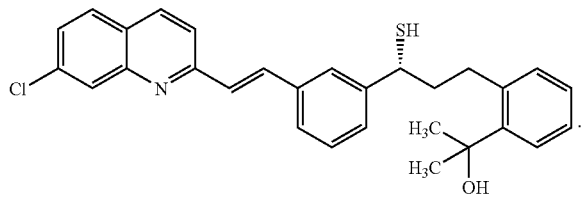

2. The process according to claim 1, wherein said cerium (III) salt is cerium trichloride.

3. The process according to claim 2, wherein said cerium salt is activated cerium trichloride.

4. The process according to claim 1, wherein said methylmagnesium halide is reacted with said compound of formula (20) or an acid addition salt thereof to produce said compound of formula (4).

5. The process according to claim 4, which further comprises:
optionally purifying said compound of formula (4); and
reacting the compound of formula (4) or a salt thereof with a compound of formula (5)

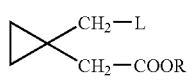
(5)

wherein R is hydrogen or a $C_1$-$C_4$ alkyl group and L is a leaving group selected from a halogen, an alkylsulfonyloxy group, and an arylsulfonyloxy group, to form a compound of formula (1a):

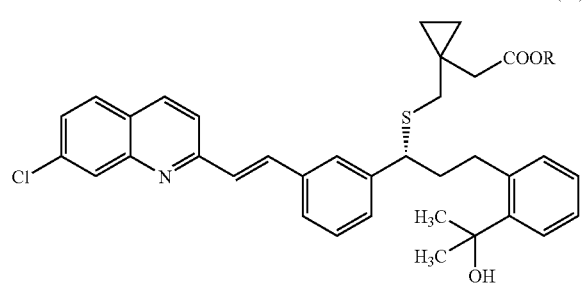
(1a)

wherein R is hydrogen or a $C_1$ to $C_4$ alkyl group.

6. The process according to claim 5, wherein R in the compound of formula (5) and (1a) is a $C_1$-$C_4$ alkyl group and wherein said process further comprises hydrolyzing said compound of formula (1a) to form a compound of formula (1):

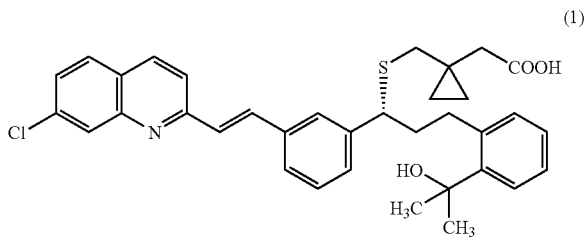
(1)

or a salt thereof.

7. The process according to claim 6, wherein said cerium (III) salt is cerium trichloride.

8. The process according to claim 6, wherein L is a p-methoxybenzene sulfonyloxy group.

9. The process according to claim 6, wherein said compound of formula (4) is subjected to said purification step which comprises crystallizing said compound of formula (4) as an acid salt.

10. The process according to claim 9, wherein said acid salt of the compound of formula (4) is formed using an acid selected from the group consisting of hydrochloric acid, toluene sulfonic acid, and benzene sulfonic acid.

11. The process according to claim 6, which further comprises purifying said compound of formula (20) before reacting said compound of formula (20) with said methylmagnesium halide.

12. The process according to claim 11, wherein said purification of said compound of formula (20) comprises converting the compound (20) into an acid addition salt selected from the group consisting of the hydrochloride, the benzenesulfonate, the p-toluenesulfonate, and the sulfate salt.

13. The process according to claim 5, which further comprises monitoring said reaction of compound (20) for a ketone of formula (12)

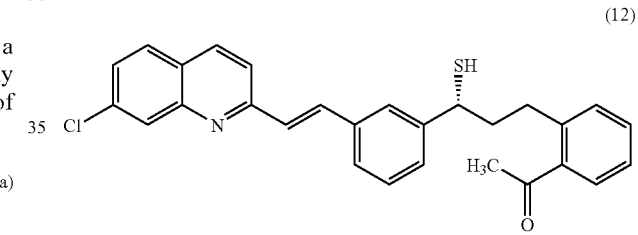
(12)

and continuing said reaction until at least said ketone is less than a predetermined limit.

14. The process according to claim 13, wherein said predetermined limit is less than 5%.

15. A process of chemical synthesis, which comprises reacting a methylmagnesium halide with a compound of formula (2a)

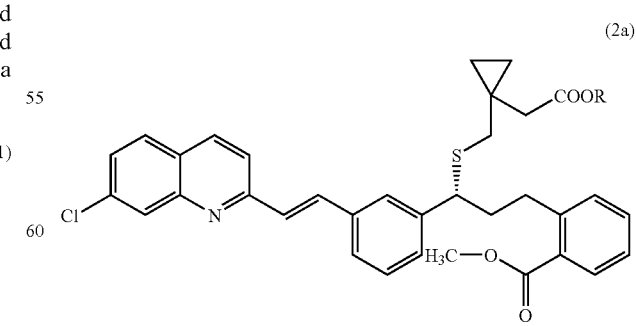
(2a)

or an acid addition salt thereof in the presence of a cerium (III) salt, to produce a compound of formula (1a):

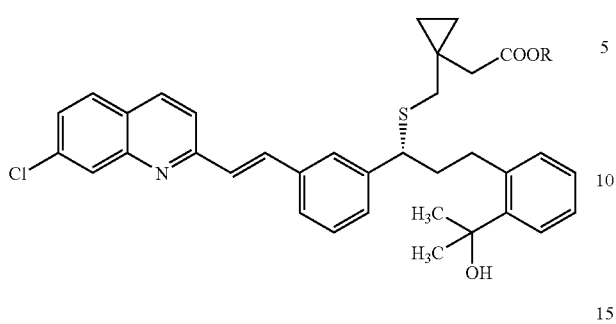

wherein R in the compound of formula (2a) and (1a) is hydrogen or a $C_1$ to $C_4$ alkyl group.

16. The process according to claim 15, wherein R in the compound of formula (2a) and (1a) is a C1-C4 alkyl group and wherein said process further comprises hydrolyzing said compound of formula (1a) to form a compound of formula (1):

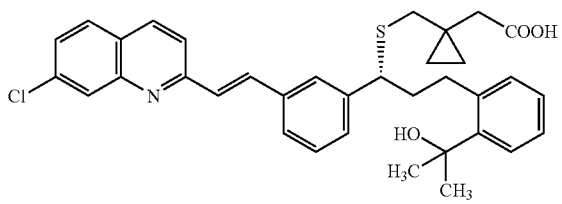

or a salt thereof.

17. The process according to claim 16, wherein said cerium (III) salt is cerium trichloride.

18. The process according to claim 15, which further comprises monitoring said reaction of compound (2a) for a ketone of formula (13) or (14)

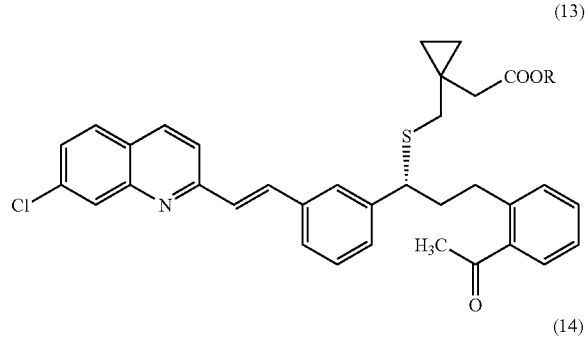

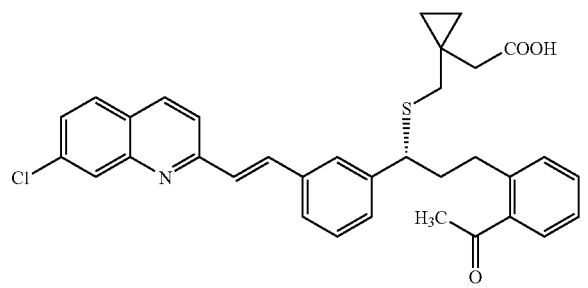

and continuing said reaction until at least said ketone is less than a predetermined limit.

19. The process according to claim 18, wherein said predetermined limit is less than 5%.

* * * * *